United States Patent [19]

Funk et al.

[11] Patent Number: 4,713,774
[45] Date of Patent: Dec. 15, 1987

[54] ALKYLATION REACTOR QUALITY CONTROL

[75] Inventors: Gary L. Funk; William B. Bard, both of Bartlesville, Okla.

[73] Assignee: Phillips Petroleum Company, Bartlesville, Okla.

[21] Appl. No.: 839,245

[22] Filed: Mar. 13, 1986

[51] Int. Cl.⁴ .................... G05D 11/13; G05D 21/02
[52] U.S. Cl. .................... 364/500; 364/173; 422/62; 585/701
[58] Field of Search ............ 364/500, 173, 473, 496; 585/701; 422/62

[56] References Cited

U.S. PATENT DOCUMENTS

| | | | |
|---|---|---|---|
| 2,881,235 | 4/1959 | Van Pool | 585/701 |
| 3,002,818 | 10/1961 | Berger | 23/253 |
| 3,018,310 | 1/1962 | Van Pool | 260/638.48 |
| 3,200,883 | 8/1965 | Phillips | 260/683.4 |
| 3,497,449 | 2/1970 | Urban | 364/173 X |
| 3,676,066 | 7/1972 | Pennington | 364/173 X |
| 4,272,823 | 6/1981 | Pool | 364/173 X |
| 4,276,257 | 6/1981 | Dixon et al. | 364/500 X |
| 4,290,110 | 9/1981 | Makovec | 364/173 X |
| 4,332,590 | 6/1982 | Smith | 422/62 X |
| 4,482,969 | 11/1984 | Funk et al. | 364/500 |
| 4,621,062 | 11/1986 | Stewart et al. | 354/500 X |

Primary Examiner—R. R. Kucia
Attorney, Agent, or Firm—George E. Bogatie

[57] ABSTRACT

In an acid alkylation process wherein a fresh isobutane stream is combined with an olefin stream to form a combined isobutane olefin feed stream, a control system maintains a desired ratio of isobutane to olefin in the combined feed stream by manipulating the flow rate of the fresh isobutane stream. In addition, the controller automatically compensates for the effect of changes in the fresh isobutane feed stream by making equal changes in the flow rate of reactor effluent. Thus, the liquid level in the alkylation reactor is unaffected by changes made in the fresh isobutane stream to maintain the desired isobutane to olefin ratio.

9 Claims, 2 Drawing Figures

ALKYLATION REACTOR QUALITY CONTROL

This invention relates to controlling an alkylation process. In one aspect this invention relates to control of the isoparaffin-to-olefin ratio in the feed stream flowing to an alkylation reactor. In another aspect, it relates to apparatus for providing a predictive signal to promptly compensate for variations in a feed stream flowing to the alkylation reactor.

BACKGROUND

Alkylation is a process technology in which low molecular weight olefins, too volatile to be used in gasoline, can be combined with an isoparaffin to make high octane motor fuel. The isoparaffin commonly alkylated is isobutane although isopentane could be utilized if desired. The most commonly used olefins are propylene and butylenes with amylenes being used less frequently. As used herein, the term butylenes refers to 1-butene, cis-2-butene, trans-2-butene and isobutylene. An acid catalyst such as hydrofluoric (HF) or sulfuric serves to catalyze the reaction. The invention will be described hereinafter in terms of the use of HF acid but is not limited to such use.

Although HF alkylation is considered by many to be a mature refining technology, many new plants are being constructed. The phase-down of lead as an octane enhancer has renewed a demand for processes such as HF alkylation which offers cost effective octane enhancement.

In a well proven alkylation process isobutane is catalytically alkylated with butylene using liquid hydroflouric acid as the catalyst, to produce a high octane motor gasoline product, or a light alkylate suitable for aviation gasoline blending. In this process the saturated isobutane feed combined with the olefin feed, usually obtained from a catalytic cracking unit, passes through feed driers. Downstream of the driers the feed mixture, olefin and isobutane, is combined with recycle isobutane. This mixture then flows to the alkylation reactor. In the reactor, the hydrocarbon feed mixture is highly dispersed into a moving bed of liquid HF catalyst where product alkylate is formed.

From the reaction zone, the hydrocarbon components and the catalyst flow upward to a settling zone. Here the catalyst breaks out as a bottom phase and flows by gravity through a cooler back to the reaction zone, where the previous cycle is repeated. The hydrocarbon phase from the settling zone, containing propane, isobutane, normal butane and alkylate, is charged to a fractionation system where the products including alkylate, propane and normal butane are separated. Isobutane is recycled to the alkylation reactor.

Generally, the octane number of the alkylate is the criterion utilized to judge the quality of the product from the alkylation process. It is known in the art that several parameters influence this octane number. Reaction temperature, acid to hydrocarbon ratio, stream impurities and isoparaffin-to-olefin ratio are all important parameters. The change in any of these parameters can affect the octane-number of the alkylate produced.

In order to maintain a desired isoparaffin-to-olefin ratio it has been proposed to analyze on line each component of the feed stream comprising fresh isobutane, recycle isobutane and olefin which typically forms the combined feed stream to the reactor, and/or to analyze an individual fresh isobutane stream and an olefin stream prior to the combining of the streams. A ratio controller is then provided to adjust the flow of one or more of the feed streams in response to the analysis ratio so that the isoparafin and olefins supplied to the reactor can be maintained at a desired ratio.

While the above described control method which manipulates the flow of one or more of the individual feed streams in response to the measured analysis ratio has proved effective for controlling the isobutane-to-olefin ratio under normal conditions, it is subject to certain limitations. For example, several parameters, such as isobutane and olefin content of fresh olefin feed, composition of the recycle isobutane stream, and volume flow rates of these streams can vary significantly and at random times. Also, the operation of the driers in the mixing section can disturb the isobutane-to-olefin ratio. These multiple disturbances can affect the operation of a controller that manipulates a relatively low volume feed stream flowing an individual feed e.g. isobutane to the alkylation reactor, such that the actual isobutane-to-olefin ratio varies as much as ±15 percent around its set point. In addition, if significant changes in the isoparaffin feed flow to the alkylation reactor are required to maintain a desired isoparaffin-to-olefin ratio, correspondingly significant changes in the liquid level within the reactor will occur.

SUMMARY OF INVENTION

It is thus an object of this invention to provide a computer system for improving the quality of the alkylate product in an alkylation process. It is a further object of the invention to precisely control the ratio of isoparaffin-to-olefin supplied to the alkylation reactor without affecting the liquid level within the reactor. It is a further object of this invention to automatically control an alkylation process so as to promptly compensate for upsets in the isobutane-to-olefin ratio of feedstock supplied to the reactor that are caused by variations in a relatively large volume recycle isobutane stream. It is a still further object of this invention to automatically control the isoparaffin-to-olefin ratio of feedstock supplied to the alkylation reactor by manipulating both a large volume reactor effluent stream, and a feed stream of relatively constant composition.

The present invention is not dependent on the particular isoparaffin feedstock utilizes, and thus, for the sake of convenience, this particular feed will be referred to as an isobutane feed stream since the most commonly used isoparaffin is isobutane.

In accordance with the present invention, there is provided a method and apparatus for controlling an alkylation reactor in which a plurality of feedstock containing streams, at least one of which is subject to variation in concentration of a desired feedstock constituent, are combined to form a combined feed stream. In the presently preferred embodiment of this invention, the combined feed stream to the reactor, which comprises paraffin and olefin hydrocarbons, is analyzed component by component to determine the mole fraction of each component flowing in the combined streams. A digital computer is provided to accept the above-mentioned analysis data, and in addition the digital computer accepts flow measurements for the fresh isobutane stream, the combined feed stream to the reactor, and the reactor effluent stream. Utilizing the above-mentioned analysis and flow data, computer calculations provide values for the current flow rate of isobutane and the current flow rate of olefin within the combined feed stream.

Generally speaking, control of the isobutane-to-olefin ratio in the combined olefin and isobutane feed stream supplied to the reactor is accomplished by determining the flow rate of fresh isobutane required to be combined with the current flow rate of olefin to maintain a desired isobutane-to-olefin ratio. In response to this determination, flow in the reactor effluent stream is adjusted by an amount equal to the difference, if any, between the required fresh isobutane flow and the actual current fresh isobutane flow. Concurrently, the fresh isobutane feed flow is adjusted by an amount equal to the amount that the reactor effluent stream was adjusted. It is noted that adjustment of the two above-mentioned flow rates is in the same sense, that is, if reactor effluent flow is increased, fresh isobutane flow is also increased and vice versa, whereby the level of liquid within the alkylation reactor is unaffected by flow rate changes required to maintain a desired ratio of reactants in the combined feed stream.

DETAILED DESCRIPTION OF THE INVENTION

Figure 1:
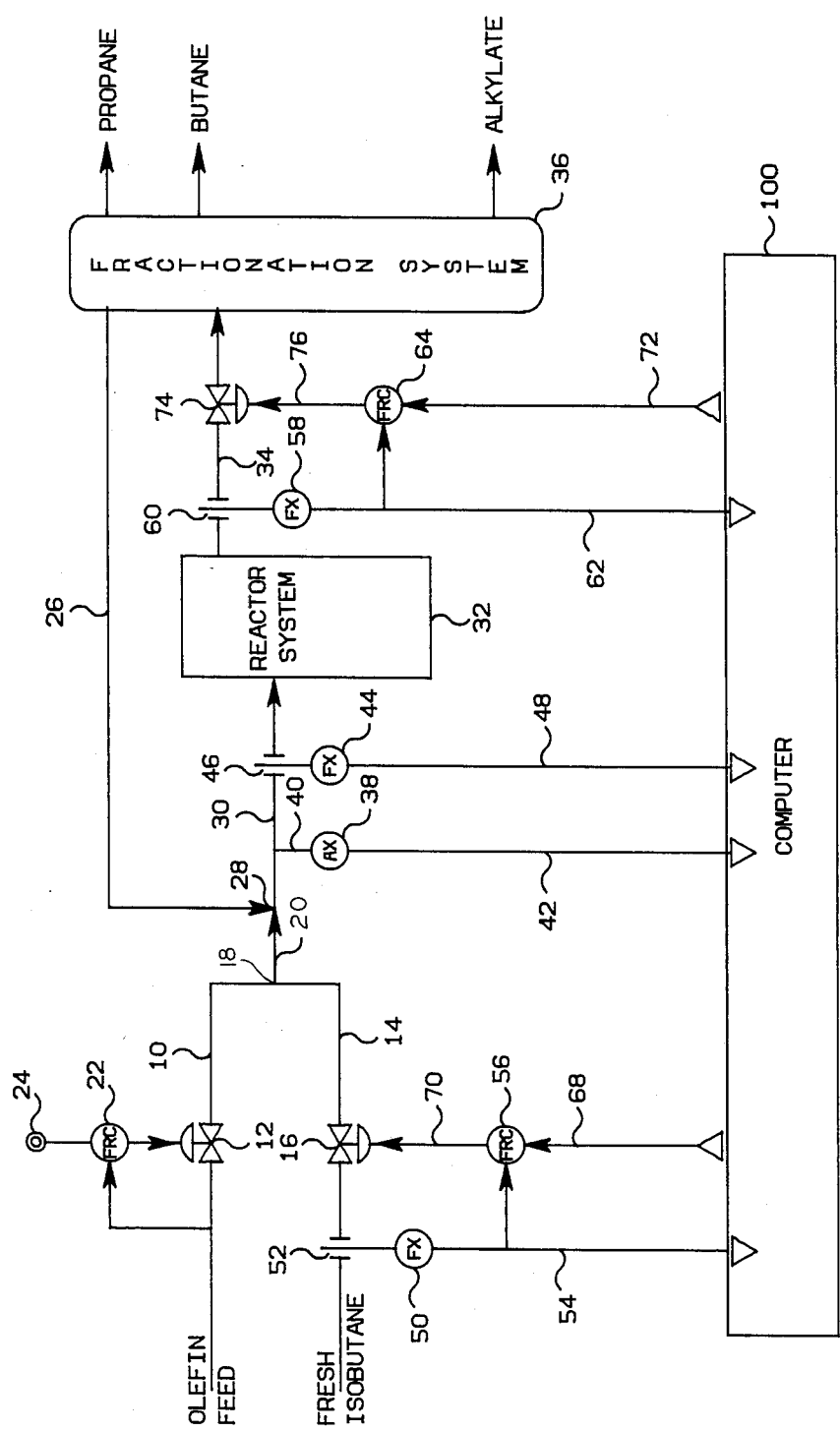
Figure 2:
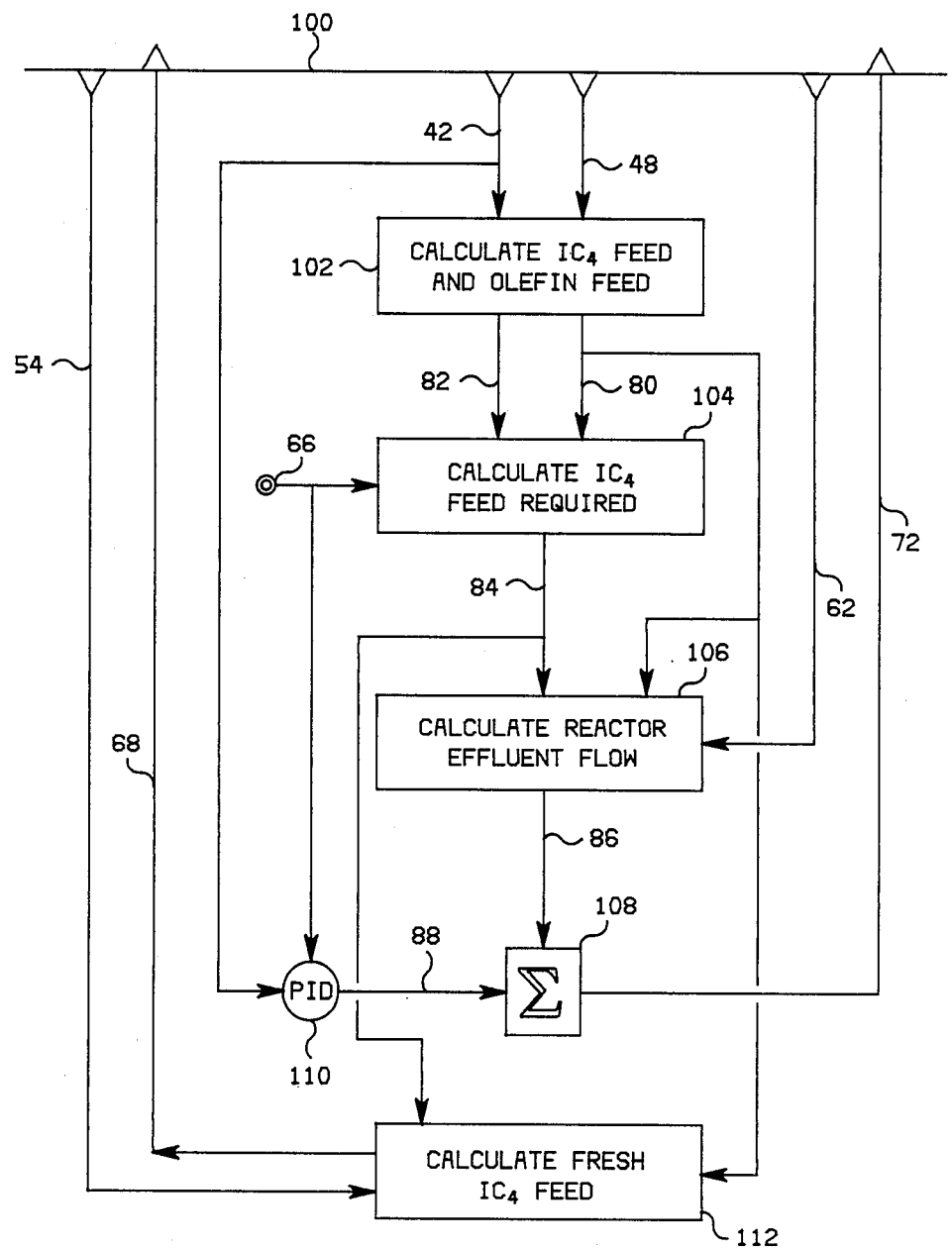

Other objects and advantages of the invention will be apparent from the foregoing brief description of the invention and the claims as well as the detailed description of the drawings in which:

FIG. 1 is a diagrammatic illustration of an alkylation reactor system together with the associated isobutane to olefin ratio control system of the present invention; and FIG. 2 is a computer flow diagram illustrating the generation of control signals utilized in the control of the alkylation process illustrated in FIG. 1.

The invention is illustrated in terms of a very simple alkylation reactor configuration in which olefin, a fresh isobutane, and a recycle isobutane are combined and provided to the alkylation reactor separate from the acid stream. In some alkylation processes, the olefin and isobutane combined streams may be combined with the acid stream before being provided to the alkylation reactor. The present invention is not limited to any particular alkylation reactor configuration but is rather applicable to any alkylation reactor in which it is possible to manipulate the flow rate of the various streams.

A specific control system configuration is set forth in FIG. 1 for the sake of illustration. However, the invention extends to different types of control system configurations which accomplish the purpose of the invention. Lines designated as signal lines in the drawings are electrical or pneumatic in this preferred embodiment. Generally, the signals provided from any transducer are electrical in form. However, the signals provided from flow sensors will generally be pneumatic in form. Transducing of these signals is not illustrated for the sake of simplicity because it is well known in the art that if a flow is measured in pneumatic form it must be transduced to electrical form if it is to be transmitted in electrical form by a flow transducer. Also, transducing of the signals from analog form to digital form or from digital form to analog form is not illustrated because such transducing is also well known in the art.

The invention is also applicable to mechanical, hydraulic or other signal means for transmitting information. In almost all control systems some combination of electrical, pneumatic, mechanical or hydraulic signals will be used. However, use of any other type of signal transmission, compatible with the process and equipment in use, is within the scope of the invention.

A digital computer is used in the preferred embodiment of this invention to calculate the required control signal based on measured process parameters as well as set points supplied to the computer. Analog computers or other types of computing devices could also be used in the invention. The digital computer is preferably an OPTROL ®7000 Process Computer System from Applied Automation, Inc., Bartlesville, Okla.

Signal lines are also utilized to represent the results of calculations carried out in a digital computer and the term "signal" is utilized to refer to such results. Thus, the term signal is used not only to refer to electrical currents or pneumatic pressures but is also used to refer to binary representations of a calculated or measured value.

The controllers shown may utilize the various modes of control such a proportional, proportional-integral-derivative. In this preferred embodiment, proportional-integral-derivative controllers are utilized but any controller capable of accepting two input signals and producing a scaled output signal, representative of a comparison of the two input signals, is within the scope of the invention.

The scaling of an output signal by a controller is well known in control system art. Essentially, the output of a controller may be scaled to represent any desired factor or variable. An example of this is where a desired flow rate and an actual flow rate is compared by a controller. The output could be a signal representative of a desired change in the flow rate of some gas necessary to make the desired and actual flows equal. On the other hand, the same output signal could be scaled to represent a temperature change required to make the desired and actual flows equal. If the controller output can range from 0 to 10 volts, which is typical, then the output signal could be scaled so that an output signal having a voltage level of 5.0 volts corresponds to 50 percent, some specified flow rate, or some specified temperature.

The various transducing means used to measure parameters which characterize the process and the various signals generated thereby may take a variety of forms or formats. For example, the control elements of the system can be implemented using electrical analog, digital electronic, pneumatic, hydraulic, mechanical or other similar types of equipment or combinations of one or more such equipment types. While the presently preferred embodiment of the invention preferably utilized a combination of pneumatic final control elements in conjunction with electrical analog signal handling and translation apparatus, the apparatus and method of the invention can be implemented using a variety of specific equipment available to and understood by those skilled in the process control art. Likewise, the format of the various signals can be modified substantially in order to accommodate signal format requirements of the particular installation, safety factors, the physical characteristics of the measuring or control instruments and other similar factors. For example, a raw flow measurement signal produced by a differential pressure orifice flow meter would ordinarily exhibit a generally proportional relationship to the square of the actual flow rate. Other measuring instruments might produce a signal which is proportional to the measured parameter, and still other transducing means may produce a signal which bears a more complicated, but known, relationship to the measured parameter. Regardless of the signal format or the exact relationship of the signal to the parameter which it represents, each signal representative of a measured process parameter or representative of a desired process value will bear a relationship to the measured parameter or desired value which permits designation of a specific measured or desired value by a specific signal value. A signal which is representative of a process measurement or desired process value is therefore one from which the information regarding the measured or desired value can be readily retrieved regardless of the exact mathematical relationship between the signal units and the measured or desired process units.

Referring now to FIG. 1, there is illustrated a feed stream containing olefins flowing through conduit means 10 which has a flow control valve 12, and an isobutane containing feed stream flowing through conduit means 14 which has a flow control valve 16. The conduits 10 and 14 are adapted to provide flow of feedstock material through their associated control valves 12 and 16 respectively to a junction point 18 where they combine to form a combined olefin and isobutane stream. Depending on the nature of the stream to be combined at the junction 18, there may be located at the junction point 18 a mixing tee or other suitable mixing means to insure that the material flowing through conduit 20 is substantially homogeneous. In the preferred embodiment illustrated, the material carried through the conduit means 10 is a stream containing olefins from a fluidic catalytic cracking unit. The flow rate is feed conduit means 10 is kept at a constant value by means of flow controller 22 which operates flow control valve 12 responsive to a set point input 24.

The feed material flowing through conduit means 14 is fresh isobutane which is typically delivered from bulk storage and is therefore not particularly subject to uncontrollable variations in overall composition.

The combined isobutane and olefin stream flowing through conduit 20 is further combined at the junction 28 with a predominately isobutane recycle stream flowing through conduit means 26. A mixing tee or other suitable mixing means may be located at junction point 28 to insure a homogeneous mixture of material flowing through conduit 30. The material flowing through conduit means 30 is the combined feed stream for alkylation reactor system 32. Reactants are removed from the reaction system 32 via conduit means 34. The reactor effluent stream flowing through conduit means 34 is provided to fractionation system 36.

The reactor configuration illustrated in FIG. 1 is a typical reactor configuration. For the sake of convenience in illustrating the invention only a very basic reactor configuration has been illustrated. Other process streams which might be provided to or withdrawn from the reactor system 32, additional process equipment such as pumps, heat exchangers, etc. and additional control components which might be associated with the alkylation reactor have not been illustrated since the additional features do not play any part in the description of the present invention. Likewise, the fractionation system 36 illustrated in FIG. 1 is illustrated as a very basic fractionation configuration. Other process streams which might be associated with a fractionation system 36, and additional process equipment such as reboilers, accumulators, etc. and additional control components which might be associated with the fractionation system have not been illustrated since such additional features play no part in the description of the present invention.

Essentially, a number of process measurements are made with the values of these process measurements being provided to a digital computer. In response to the process measurements and operator supplied set points, the digital computer provides two output control signals which are utilized to manipulate two process streams in such a manner as to maintain the isobutane to olefin ratio in the feed stream flowing through conduit 30 essentially equal to the desired isobutane to olefin ratio. The process measurements will first be described and then the manner in which the control signals are utilized to control the alkylation reactor will be described. Thereafter, a detailed description of the manner in which the process measurements are utilized to derive the control signals will be provided.

Analyzer transducer 38 which is preferably a chromatographic analyzer such as the OPTICHROM-®ADVANCE analyzer from Applied Automation Incorporated, Bartlesville, Okla., is in fluid communication with conduit means 30 via conduits means 40. Analyzer transducer 38 provides an output signal 42 which is a plurality of signals representative of the concentration of a plurality of components in the combined feed stream flowing in conduit means 30. The components analyzed by analyzer transducer 38 include at least $IC_4$, $C_3$ olefins, $C_4$ olefins, $C_5$ olefins, and the isobutane/olefin ratio. Signal 42 is provided from analyzer transducer 38 as an input signal to computer 100 where the plurality of signals from analyzer 38 are transferred sequentially to the computer 100. The values of the plurality of signals 42 are periodically updated.

Flow transducer 44 in combination with flow sensor 46 which is operably located in conduit means 30 provides an output signal 48 which is representative of the actual flow rate of the feed stream flowing through conduit means 30. Signal 48 is provided from the flow transducer 44 as an input signal to computer 100.

Flow transducer 50 in combination with flow sensor 52 which is operably located in conduit means 14 provides an output signal 54 which is representative of the actual flow rate of the fresh isobutane feed stream flowing through conduit means 14. Signal 54 is provided from the transducer 50 as the process variable input to the flow controller 56 and also as an input signal to computer 100. In like manner flow transducer 58 in combination with flow sensors 60 which is operably located in conduit means 34 provides an output signal 62 which is representative of the actual flow rate of the reactor effluent stream flowing through conduit means 34. Signal 62 is provided from flow transducer 58 as a process variable to flow controller 64 and as an input signal to computer 100.

As has been previously stated, computer 100 outputs two control signals in response to the above-described process measurements and an operator entered set point signal 66 illustrated in FIG. 2 which is representative of the desired isobutane-to-olefin ratio for the material flowing as feed in conduit means 30. Signal 68 which is provided from computer 100 as a set point signal to flow controller 56 is representative of the flow rate of the isobutane-containing stream flowing through conduit means 14 required to maintain a desired isobutane/olefin ratio in the combined feed stream flowing through conduit means 30. In response to signal 68 and 54, the flow controller 56 provides an output signal 70 which is responsive to the difference between signals 54 and 68.

Signal 70 is scaled so as to be representative of the position of the control valve 16 which is operably located in conduit means 14, required to maintain the actual flow rate of the isobutane-containing stream flowing through conduit means 14 substantially equal to the flow rate represented by signal 68. Signal 70 is provided from the flow controller 56 as a control signal to control valve 16 and the control valve 16 is manipulated in response thereto.

Signal 72 which is provided from the computer 100 as the set point signal to flow controller 64 is representative of the flow rate of the reactor effluent stream flowing through conduit means 34 which will offset flow changes in isobutane feed by corresponding changes in the flow rate of the reactor effluent stream flowing in conduit means 34. Thus, if an increase or decrease in the flow rate of the isobutane-containing fluid stream 14 is required to maintain the desired isobutane-to-olefin ratio in the combined feed stream 30, an equal change is made in the reactor effluent stream 34. In this manner, the liquid level in reactor 32 is unaffected by changes in flow rate in conduit means 14. In response to signals 62 and 72, the flow controller 64 provides an output signal 76 which is responsive to the difference between signal 62 and 72. Signal 76 is scaled so as to be representative of the position of control valve 74 required to maintain the actual flow rate in conduit means 34 substantially equal to the flow rate represented by signal 72. Signal 76 is provided from a flow controller 64 as a control signal to control valve 74 and control valve 74 is manipulated in response thereto.

The computer flow diagram utilized to calculate the control signals 68 and 72 in response to the previously described input signals to computer 100 and in response to a set point 66 which is also provided to computer 100 is illustrated in FIG. 2. Referring now to FIG. 2, signal 48 which is representative of the flow rate in conduit means 30 is provided to the calculate isobutane feed and olefin feed computer block 102. The computer block 102, which can be a computer software subroutine, is also provided with signal 42 which as previously stated is representative of a plurality of component concentrations of fluid flowing through conduit means 30 including the concentration of isobutane and olefin. In response to the concentration of isobutane as determined by analyzer 38 and the flow rate in conduit means 30, the computer block 102 calculates the flow rate of actual isobutane within the combined feed stream 30 in accordance with the formula $$F_i = (MP/100)(58.120/MW_t)(F_c)$$

where
$F_i$ = flow rate of actual isobutane in the combined feed stream flowing in conduit means 30, lb/hr
MP = mole percent of isobutane in the combined feed stream as determined by analyzer 38,
$MW_t$ = average molcular weight of combined feed stream as determined in response to analyzer 38, lb/mole
$F_c$ = flow rate of combined feed stream as determined by flow transducer 44, lb/hr The computer block 102 provides an output signal 80 which is representative of the actual flow rate of isobutane flowing within conduit means 30. In a similar manner, computer block 102 provides an output signal 82 which is representative of the actual flow rates of $C_3$, $C_4$, and $C_5$ olefins flowing within conduit means 30.

Signals 80 and 82 are provided from the calculate isobutane and olefin feed computer block 102 as inputs to the calculate isobutane feed required computer block 104. Computer block 104 is also provided with the set point signal 66 which is representative of the desired isobutane to olefin ratio of the fluid flowing in conduit means 30. The desired isobutane/olefin ratio of the combined feed stream flowing through conduit 30 will generally be well known for a particular alkylation process and can be entered by an operator. In response to these described inputs, computer block 104 calculates the isobutane feed flowing in conduit means 30 required to maintain the actual isobutane-to-olefin ratio of reactants flowing in conduit means 30 substantially equal to the desired isobutane-to-olefin ratio represented by signal 66 in accordance with the formula $$F_{ir} = MR(F_{c3}/42.078 + F_{c4}/56.104 + F_{c5}/70.130)$$
$$(58.120)$$

where
$F_{ir}$ = flow rate of isobutane required in conduit means 30 to maintain the desired ratio of reactants in the combined feed stream, lb/hr
MR = desired ratio of isobutane of olefin, mole isobutane/mole olefin
$F_{C3}$ = flow rate of $C_3$ olefins in combined feed stream determined by computer block 102, lb/hr
$F_{c4}$ = flow rate of $C_4$ olefins in combined feed stream as determined by computer block 102 lb/hr
$F_{c5}$ = flow rate of $C_5$ olefins in combined feed stream as determined by computer block 102, lb/hr.

The computer block 104 provides an output signal 84 which is representative of the flow rate of isobutane flowing through conduit means 30 required to maintain the actual isobutane/olefin ratio in the combined feed stream flowing through conduit means 30 substantially equal to the desired isobutane-to-olefin ratio represented by signal 66.

Signal 84 is provided from the calculate isobutane feed required computer block 104 as an input signal to calculate reactor effluent computer block 106. Computer block 106 is also provided with signal 62 which is representative of the actual flow rate in conduit means 34, as determined by transducer 58, and signal 80 which is representative of the actual flow rate of isobutane flowing in conduit means 30. In response to these described inputs, computer block 106 calculates the flow rate of the reactor effluent stream flowing in conduit means 34 which will offset flow changes in fresh isobutane feed by corresponding changes in the flow rate of the reactor effluent stream, in accordance with the formula:

$$F_{er} = F_{ec} + (F_{ir} - F_i)$$

where
$F_{er}$ = flow rate of reactor effluent stream which will offset flow changes in fresh isobutane feed by corresponding changes in the combined feed stream,
$F_{ec}$ = flow rate of reactor effluent stream as determined by flow transducer 58,
$F_{ir}$ and $F_i$ are as previously defined.

The computer block 106 provides an output signal 86 which is representative of the flow rate of the reactor effluent stream flowing in conduit means 34 which will offset flow changes in the isobutane feed by corresponding changes in the reactor effluent stream. Signal 86 is generally predictive in nature because it is based on calculations involving known molecular weights of components, and measured flow rates and component concentrations. Signal 68 is provided from the calculate reactor effluent flow rate computer block 106 as an input to summing block 108. Signal 66 which is representative of the desired isobutane-to-olefin ratio of the a fluid flowing in conduit means 30 is provided as a set point signal to controller block 110. Controller block 110, which can be a computer software subroutine, is also provided with a process variable input by signal 42. Signal 42 as has been previously stated is representative of a plurality of signals including the actual isobutane-/olefin ratio of the combined feed stream flowing in conduit means 30. In response to the actual isobutane-/olefin ratio supplied from signal 42 and the desired isobutane/olefin ratio represented by signal 66, a controller block 110 provides an output signal 88 which is responsive to the difference between signals 42 and 66. Signal 88 is scaled so as to be representative of any change in the flow rate represented by signal 86 required to make the actual analysis represented by signal 42 substantially equal to the set point represented by signal 66. Signal 88 is a feedback or trim factor. Essentially, if the predictive control signal based on signal 86 is maintaining the desired isobutane/olefin ratio in the feed stream flowing through conduit means 30, signal 88 will have magnitude of zero. Only when the predictive control fails to maintain the desired isobutane-to-olefin ratio will the trim factor represented by signal 88 become effective. Signal 88 is provided from the controller block 110 as a second input to the summing block 108. Signals 86 and 88 are summed to establish signal 72 which is provided as a control signal from the computer 100 and is utilized as previously described.

Signal 84, which is the isobutane flow required to maintain the desired ratio represented by signal 66, is also provided from the computer block 104 as an input signal to the calculate fresh isobutane feed computer block 112. Also provided to computer block 112 is signal 54 which is representative of the actual flow rate in conduit means 14, and signal 80 from computer block 102 which is representative of the actual isobutane flow rate in conduit means 30. In response to these described inputs, computer block 112 calculates the flow rate of the isobutane containing stream flowing in conduit means 14 required to maintain the desired isobutane-to-olefin ratio in accordance with the formula $$F_{if} = F_{ic} + (F_{ir} - F_i)$$

$F_{if}$=flow rate of fresh isobutane feed flowing in conduit means 14 required to maintain the desired isobutane/olefin ratio set point represented by signal 66, lb/hr $F_{ic}$=flow rate of fresh isobutane containing fluid stream as determined by flow transducer 50, lb/hr $F_{ir}$ and $F_i$ are as previously defined.

The computer block 112 provides an output signal 68 which is representative of the flow rate of the fresh isobutane containing stream flowing in conduit means 14 which is required to maintain the actual isobutane to olefin ratio in the combined feed stream flowing in conduit means 30, substantially equal to the desired isobutane to olefin ratio represented by signal 66. Signal 68 is provided as a control signal from computer 100 and is utilized as previously described.

The invention has been described in terms of a presently preferred embodiment as illustrated in FIGS. 1 and 2. Specific components which can be utilized in the practice of the invention as illustrated in FIGS. 1 and 2 such as flow sensors 52, 46 and 60; flow transducer 50, 44 and 58; flow controllers 56, 64 and 22; are each well known, commercially available control components such as are described at length in Perry's Chemical Engineers Handbook, 4th Edition, Chapter 22, which is available from McGraw Hill.

While the invention has been described in terms of the presently preferred embodiment, reasonable variations and modifications are possible by those skilled in the art and such modifications are within the scope of the described invention and the appended claims.

That which is claimed is:

1. Apparatus comprising:

an alkylation reactor;

a fractional distillation column means;

means for withdrawing a mixture containing unreacted isoparaffin as a reactor effluent stream from said alkylation reactor, and for providing said reactor effluent stream as a feed to said fractional distillation column means wherein at least a portion of said unreacted isoparaffin is separated to form a predominately isoparaffin containing recycle stream;

means for combining an isoparaffin-containing fluid stream with an olefin-containing fluid stream to form a combined isoparaffin and olefin stream;

means for combining said recycle stream and said combined paraffin and olefin stream to form a combined feed stream and for providing said combined feed stream to said alkylation reactor;

means for establishing a first signal representative of the desired isoparaffin-to-olefin ratio in said combined feed stream;

means for establishing a second signal representative of the flow rate of said combined feed stream;

means for establishing a third signal representative of the flow rate of said isoparaffin-containing fluid stream;

means for establishing a fourth signal representative of the flow rate of said reactor effluent stream;

analyzer means for detecting the concentration of olefin supplied through said combined feed stream, and for detecting the concentration of isoparaffin supplied through said combined feed stream, and for detecting the molecular weight of said combined feed stream;

computer means responsive to said analyzer means and to said first, second, third and fourth signals for calculating a first control signal which is representative of the flow rate of said isoparaffin containing fluid stream required to maintain the actual isoparaffin to olefin ratio in said combined feed stream substantially equal to the desired isoparaffin to olefin ratio represented by said first signal, and for calculating a second control signal which is representative of the flow rate of said reactor effluent stream which will offset flow changes in said isoparaffin containing fluid stream by corresponding flow changes in said reactor effluent stream, whereby the liquid level in said alkylation reactor will be unaffected by changes in the flow rate of said isoparaffin containing fluid stream required to maintain the ratio represented by said first signal;

means for manipulating the flow rate of said isoparaffin containing fluid stream in response to said first control signal, to thereby maintain the actual isoparaffin to olefin ratio in said combined feed stream substantially equal to the ratio represented by said first signal;

means for manipulating the flow rate of said reactor effluent stream in response to said second control signal, to thereby maintain the liquid level in said alkylation reactor essentially constant.

2. Apparatus in accordance with claim 1 additionally comprising:

analyzer means for establishing a fifth signal representative of the actual isoparaffin-to-olefin ratio of fluid supplied through said combined feed stream;

computer means for comparing said first signal and said fifth signal and for establishing a sixth signal which is responsive to the difference between said first signal and said fifth signal, wherein said sixth signal is scaled so as to be representative of any change in magnitude of said first control signal required to maintain the actual isoparaffin to olefin ratio represented by said fifth signal substantially equal to the desired isoparaffin to olefin ratio represented by said first signal; and computer means for combining said sixth signal and said first control signal, wherein said first control signal as modified by said sixth signal is utilized to manipulate the flow rate of said reactor effluent stream.

3. Apparatus in accordance with claim 2 wherein said computer means for combining said sixth signal and said first control signal comprises a summing means.

4. Apparatus in accordance with claim 1 wherein said analyzer means determines the concentration of olefins in said combined feed stream by analyzing said feed stream for the concentration of $C_3$ olefins, $C_4$ olefins and $C_5$ olefins.

5. A method for controlling an alkylation reactor wherein an olefin containing feed stream is combined with an isoparaffin containing feed stream, and the combined olefin and isoparaffin feed stream is further combined with a predominately isoparaffin recycle stream to form a combined feed stream, with said combined feed stream being provided to said alkylation reactor, and wherein a stream containing unreacted isoparaffin is withdrawn from said reactor to form a reactor effluent stream which is passed to a fractionation column, said method comprising the steps of:

establishing a first signal representative of the desired isobutane to olefin ratio in said combined feed stream;

establishing a second signal representative of the flow rate of said combined feed stream;

establishing a third signal representative of the flow rate of said isoparaffin containing feed stream;

establishing a forth signal representative of the flow rate of said reactor effluent stream;

analyzing said combined feed stream to determine the concentration of isoparaffin and the concentration of olefins in said combined feed stream, and to determine the molecular weight of said combined feed stream;

establishing a first control signal representative of the flow rate of said isoparaffin containing feed stream required to maintain the actual isoparaffin to olefin ratio substantially equal to the ratio represented by said first signal;

establishing a second control signal representative of the flow rate of said reactor effluent stream which will offset flow changes in said isoparaffin containing feed stream by corresponding flow changes in said reactor effluent stream, whereby the liquid level in said alkylation reactor will be unaffected by changes in the flow rate of said isoparaffin containing feed stream required to maintain the actual ratio of isoparaffin to olefin substantially equal to the ratio represented by said first signal;

manipulating the flow rate of said isoparaffin containing feed stream in response to said first control signal, to thereby maintain the actual isoparaffin to olefin ratio in said combined feed stream substantially equal to the ratio represented by said first signal; and manipulating the flow rate of said reactor effluent stream in response to said second control signal.

6. A method in accordance with claim 5 additionally comprising the steps of:

analyzing said combined feed stream to establish a fifth signal representative of the actual isobutane to olefin ratio of fluid supplied through said combined feed stream;

comparing said first signal and said fifth signal to establish a sixth signal which is responsive to the difference between said first signal and said fifth signal, wherein said sixth signal is scaled so as to be representative of any changes in the magnitude of said first control signal required to maintain the actual isoparaffin to olefin ratio represented by said fifth signal substantially equal to the ratio represented by said first signal; and combining said sixth signal and said first control signal wherein said first control signal as modified by saidسعید sixth signal is utilized to manipulate the flow rate of said reactor effluent stream.

7. A method in accordance with claim 5 wherein analyzing said combined feed stream to determine the concentration olefins comprises:

analyzing for the concentration of $C_3$ olefins, $C_4$ olefins and $C_5$ olefins.

8. A method in accordance with claim 7 wherein the step of establishing a first control signal representative of the flow rate of said isoparaffin containing stream required to maintain the actual isoparaffin to olefin ratio substantially equal to the ratio represented by said first signal includes the following steps:

programming a computer to calculate the flow rate of isobutane in said combined feed stream essentially according to the formula $$F_i = (MP/100)(58.120/MW_t)(F_c)$$

where
$F_i$ = flow rate of isobutane in said combined feed stream, lb/hr
$MP$ = mole percent of isobutane in said combined feed stream
$MW_t$ = average molecular weight determined from analyzing said combined feed stream, and
$F_c$ = flow rate of combined feed stream as represented by said second signal, and further programming said computer to calculate the required flow rate of isobutane within said combined feed stream essentially according to the formula $$F_{ir} = (MR)(F_{c3}/42.078 = F_{c4}/56.104 + F_{c5}/70.130)(58.120)$$

where $F_{ir}$ = flow rate of isobutane within said combined feed stream required to maintain the actual isobutane to olefin ratio of said combined feed stream essentially equal to the ratio represented by said first signal, lb/hr MR = mole ratio of reactants as represented by said first signal, $FC_3$ = flow rate of $C_3$ olefins in said combined feed stream, lb/hr $FC_4$ = flow rate of $C_4$ olefins in said combined feed stream, lb/hr $FC_5$ = flow rate of $C_5$ olefins in said combined feed stream, lb/hr.

9. A method in accordance with claim 8 additionally comprising the step of:

programming said computer to calculate the flow rate of said reactor effluent stream essentially according to the formula $$F_{er} = F_{ec} + (F_{ir} - F_i)$$

where $F_{er}$ = flow rate of reactor effluent stream required to offset flow changes in said isobutane containing feed stream, lb/hr $F_{ec}$ = current flow rate of reactor effluent steam, lb/hr.

$F_{ir}$ and $F_i$ are as defined in claim 8.

* * * * *